United States Patent
Li et al.

(10) Patent No.: US 11,806,179 B2
(45) Date of Patent: Nov. 7, 2023

(54) METHODS, APPARATUSES AND SYSTEMS FOR SURVIEW SCAN

(71) Applicant: Neusoft Medical Systems Co., Ltd., Liaoning (CN)

(72) Inventors: Shuangxue Li, Liaoning (CN); Jun Yu, Liaoning (CN); Wei Li, Liaoning (CN)

(73) Assignee: Neusoft Medical Systems Co., Ltd., Shenyang (CN)

( * ) Notice: Subject to any disclaimer, the term of this patent is extended or adjusted under 35 U.S.C. 154(b) by 0 days.

(21) Appl. No.: 17/698,744

(22) Filed: Mar. 18, 2022

(65) Prior Publication Data

US 2022/0296182 A1  Sep. 22, 2022

(30) Foreign Application Priority Data

Mar. 19, 2021  (CN) .......................... 202110298276.2

(51) Int. Cl.
*A61B 6/08*  (2006.01)
*A61B 6/03*  (2006.01)
(Continued)

(52) U.S. Cl.
CPC ................ *A61B 6/08* (2013.01); *A61B 6/032* (2013.01); *A61B 6/037* (2013.01); *A61B 6/488* (2013.01);
(Continued)

(58) Field of Classification Search
CPC ........... A61B 6/08; A61B 6/032; A61B 6/037; A61B 6/488; A61B 6/547; A61B 6/0487; A61B 6/0407; G06T 7/73
See application file for complete search history.

(56) References Cited

U.S. PATENT DOCUMENTS

| | | |
|---|---|---|
| 8,995,611 B2 | 3/2015 | Durgan et al. |
| 2010/0173269 A1* | 7/2010 | Puri .................... G09B 19/0092 434/127 |

(Continued)

FOREIGN PATENT DOCUMENTS

| | | | |
|---|---|---|---|
| CN | 103079470 A | 5/2013 | |
| CN | 107456239 A | * 12/2017 | ........... A61B 6/0407 |

(Continued)

OTHER PUBLICATIONS

Office Action and Search Report Issued in Chinese Application No. 2021102982762, dated Oct. 19, 2022, 20 pages (with Machine/Partial Translation).

*Primary Examiner* — David P Porta
*Assistant Examiner* — Casey Bryant
(74) *Attorney, Agent, or Firm* — Fish & Richardson P.C.

(57) ABSTRACT

Methods, apparatuses and systems for surview scans are provided. In one aspect, a method includes: collecting an image for a subject on a scan bed of a computed tomography system when the scan bed is stationary; determining a scan beginning position for a surview scan in the image, where graduation patterns are marked on the scan bed, and a relative position between the graduation patterns and the scan bed remains unchanged; obtaining a first distance between the scan beginning position and a surview collection plane perpendicular to the scanning bed according to the graduation patterns in the image; controlling the scan bed to move toward the surview collection plane; and in response to determining that a scan bed moving distance reaches the first distance, starting the surview scan to obtain a surview image.

16 Claims, 5 Drawing Sheets

(51) Int. Cl.
*G06V 10/22* (2022.01)
*G06T 7/73* (2017.01)
*G06V 40/16* (2022.01)
*A61B 6/00* (2006.01)

(52) U.S. Cl.
CPC ............ *A61B 6/547* (2013.01); *G06T 7/73* (2017.01); *G06V 10/22* (2022.01); *G06V 40/16* (2022.01)

(56) References Cited

U.S. PATENT DOCUMENTS

| | | | |
|---|---|---|---|
| 2015/0086101 A1* | 3/2015 | Bhagalia | A61B 6/503 378/4 |
| 2016/0117826 A1 | 4/2016 | Yan | |
| 2022/0061781 A1* | 3/2022 | Zhao | G06T 7/0012 |
| 2022/0301166 A1* | 9/2022 | Li | G06V 10/25 |

FOREIGN PATENT DOCUMENTS

| | | | | |
|---|---|---|---|---|
| CN | 107456239 A | | 12/2017 | |
| CN | 108294772 A | | 7/2018 | |
| CN | 109276248 A | * | 1/2019 | ........... A61B 5/0555 |
| CN | 110123348 A | | 8/2019 | |

* cited by examiner

100 # METHODS, APPARATUSES AND SYSTEMS FOR SURVIEW SCAN

CROSS REFERENCE TO RELATED APPLICATION

This application claims priority to Chinese Patent Application No. 202110298276.2 filed on Mar. 19, 2021, the entire content of which is incorporated herein by reference for all purposes.

TECHNICAL FIELD

The present disclosure relates to the field of medical image processing technologies, and in particular to methods, apparatuses and systems for surview scan.

BACKGROUND

A Computed Tomography (CT) system includes a CT device and a main console. The CT device is located in a scan room to perform CT scan for a subject and the main console is located in an operation room to control the CT device.

The CT system performs a surview scan (may also be referred to as a localizer scan) in the following process including that: firstly, an operation technician performs subject registration and scan protocol selection in the operation room; then, the operation technician enters the scan room to allow the subject to lie on a scan bed, position the subject according to a to-be-scanned region of the subject, light up a scan positioning line of the CT device and confirm that the scan positioning line of the CT device is emitted onto a scan beginning position of a body surface of the subject; after completing the positioning, the operation technician goes back to the operation room and collects data by operating the CT device to radiate continuously; at this time, the scan bed carries the subject through a radiation region at a constant speed and a surview image (may also be referred to as a localizer image) is formed through processing.

It can be seen that, in a surview scan process, the operation technician needs to complete positioning through direct contact with the subject. If an infectious disease is carried by the subject, a great healthy risk will be brought to the operation technician.

SUMMARY

According to a first aspect of embodiments of the present disclosure, there is provided a method applied to a computed tomography system. The method includes: collecting an image for a subject on a scan bed of the computed tomography system when the scan bed is stationary; determining a scan beginning position for a surview scan in the image, where graduation patterns are marked on the scan bed, and a relative position between the graduation patterns and the scan bed remains unchanged; obtaining a first distance between the scan beginning position and a surview collection plane perpendicular to the scanning bed according to the graduation patterns in the image; controlling the scan bed to move toward the surview collection plane; and in response to determining that a scan bed moving distance reaches the first distance, starting the surview scan to obtain a surview image.

According to a second aspect of embodiments of the present disclosure, there is provided an apparatus for a surview scan, including: a determining module, configured to collect an image for a subject on a scan bed of a computed tomography system when the scan bed is stationary, and determine a scan beginning position for a surview scan in the image, where graduation patterns are marked on the scan bed, and a relative position between the graduation patterns and the scan bed remains unchanged; an obtaining module, configured to obtain a first distance between the scan beginning position and a surview collection plane perpendicular to the scanning bed according to the graduation patterns in the image; and a scan module, configured to, controlling the scan bed to move toward the surview collection plane; and in response to determining that a scan bed moving distance reaches the first distance, start the surview scan to obtain a surview image.

According to a third aspect of embodiments of the present disclosure, there is provided a system for a surview scan, including a scan bed, a scan gantry, a camera and a main console. The scan gantry is configured to control the scan bed to move according to a control instruction of the main console. The camera is disposed above the scan bed to collect a video image of a subject on the scan bed and send the video image to the main console. The main console is configured to perform following operations comprising: collecting an image for the subject when the scan bed is stationary, and determining a scan beginning position for a surview scan in the image, where graduation patterns are marked on the scan bed, and a relative position between the graduation patterns and the scan bed remains unchanged; obtaining a first distance between the scan beginning position and a surview collection plane perpendicular to the scanning bed according to the graduation patterns in the image; controlling the scan bed to move toward the surview collection plane; and in response to determining that a scan bed moving distance reaches the first distance, starting the surview scan to obtain a surview image.

The foregoing and other aspects or embodiments can each optionally include one or more of the following features, alone or in combination. For example, the method further includes: determining a scan ending position for the surview scan in the image; obtaining a second distance between the scan ending position and the surview collection plane according to the graduation patterns in the image; and after starting the surview scan, controlling the scan bed to move toward the surview collection plane and then stopping the surview scan in response to determining that a second scan bed moving distance reaches the second distance.

In some embodiments, the method further includes: determining a surview scan length according to a selected scan protocol; and in response to determining that a second scan bed movement distance from starting the surview scan reaches the surview scan length, stopping the surview scan.

In some embodiments, the determining the scan beginning position for the surview scan in the image includes: determining the scan beginning position for the surview scan in the image according to received positioning operation information.

In some embodiments, the determining the scan beginning position for the surview scan in the image includes: recognizing a face position in the image based on a predetermined face recognition algorithm; obtaining body height information of the subject according to one or more graduation patterns corresponding to the subject in the image; extracting a target scan region from a selected scan protocol; and determining, according to the recognized face position, the body height information and the target scan region, the scan beginning position for the surview scan in the image.

In some embodiments, the obtaining the first distance between the scan beginning position and the survey collection plane perpendicular to the scanning bed according to the graduation patterns in the image includes: in response to determining that one of the graduation patterns corresponding to the scan beginning position is unobstructed in the image, determining the first distance according to a position relationship between a graduation value of the one of the graduation patterns and the survey collection plane in the image.

In some embodiments, the obtaining the first distance between the scan beginning position and the survey collection plane perpendicular to the scanning bed according to the graduation patterns in the image includes: in response to determining that one of the graduation patterns corresponding to the scan beginning position is obstructed in the image, predicting a graduation value of the one of the graduation patterns according to one or more unobstructed graduation patterns in the image; and determining the first distance according to a position relationship between the predicted graduation value and the survey collection plane in the image.

In some embodiments, the graduation patterns comprise checkerboard patterns, and in each of the checkerboard patterns, squares of two different colors are alternately disposed and an intersection of adjacent squares is a graduation point corresponding to a graduation value.

In some embodiments, different graduation values in the graduation patterns correspond to different colors.

In some embodiments, the graduation patterns are located on one of: a bed board of the scan bed, a mattress of the scan bed, a mattress cover of the scan bed, or a bed cover of the scan bed.

It should be understood that the above general descriptions and subsequent detailed descriptions are merely illustrative and explanatory rather than limiting of the present disclosure.

BRIEF DESCRIPTION OF THE DRAWINGS

The accompanying drawings, which are incorporated in and constituted a part of the present description, illustrated embodiments consistent with the present disclosure and served to explain the principles of the present disclosure together with the description.

Like reference numbers and designations in the various drawings indicate like elements. It is also to be understood that the various exemplary implementations shown in the figures are merely illustrative representations and are not necessarily drawn to scale.

DETAILED DESCRIPTION OF THE EMBODIMENTS

Example embodiments will be described in detail herein, with the illustrations thereof represented in the drawings. When the following descriptions involve the drawings, like numerals in different drawings refer to like or similar elements unless otherwise indicated. The embodiments described in the following examples do not represent all embodiments consistent with the present disclosure. Rather, they are merely examples of apparatuses and methods consistent with some aspects of the present disclosure as detailed in the appended claims.

The terms used in the embodiments of the present disclosure are for the purpose of describing particular embodiments only, and are not intended to limit the present disclosure. Terms "a," "the" and "said" in their singular forms in the embodiments of the present disclosure and the appended claims are also intended to include plurality, unless clearly indicated otherwise in the context. It should also be understood that the term "and/or" as used herein refers to and includes any or all possible combinations of one or more of the associated listed items.

It is to be understood that, although the terms "first," "second," "third," and the like may be used in the embodiments of the present disclosure to describe various information, such information should not be limited to these terms. These terms are only used to distinguish the same type of information from each other. For example, without departing from the scope of the present disclosure, the first information may also be referred to as the second information and similarly, the second information may also be referred to as the first information. Depending on the context, the word "if" as used herein may be interpreted as "when" or "upon" or "in response to determining".

A CT scan process for a subject includes two stages: in a first stage, a surview scan is performed for the subject with a lower dose radiation to obtain a surview image; and in a second stage, parameter values such as slice thickness and slice gap required for a subsequent CT scan are configured based on the surview image, where a radiation dose used in the second stage is greater than a radiation dose used in the first stage, and tomograms obtained by CT scan in the second stage can be used for disease diagnosis. In a pandemic season of infectious diseases, or in a special application scenario such as a fever clinic in a hospital, it is highly possible that a subject needing to receive a CT scan (e.g., COVID-19 patient) carries an infectious virus, which brings a large risk to the health of persons in contact with the subject. At this time, additional requirements will be proposed for use of medical appliances in a treatment or diagnosis location. Thus, it is highly desirable that an operation technician can complete an entire scan process in an operation room without entering a scan room to be in direct contact with the subject, thereby reducing the risk to the health of the operation technician.

Figure 1:
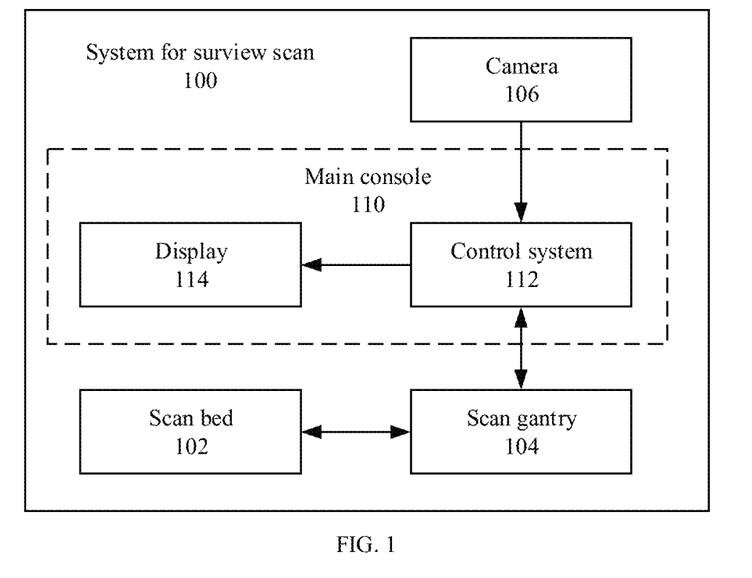
FIG. 1 is a structural example diagram illustrating a system for surview scan according to one or more embodiments of the present disclosure.

Implements of the present disclosure provide systems for surview scan, which can meet the above requirements. FIG. 1 is a structural example diagram illustrating a system 100 for surview scan according to one or more embodiments of the present disclosure.

As shown in FIG. 1, the system 100 for surview scan can include a scan bed 102, a scan gantry 104, a camera 106, and a main console 110. In some examples, the scan bed 102 and the scan gantry 104 can be a scan bed and a scan gantry in a medical imaging system, e.g., a CT system or a Positron Emission Tomography Computed Tomography (PET-CT) system.

The scan gantry 104 is configured to control the scan bed 104 to move according to a control instruction of the main console 110. The camera 106 is disposed above the scan bed 102 to collect a video image of a subject on the scan bed 102 and send the video image to the main console 110. The main console 110 is configured to implement a method of surview scan described subsequently. In some examples, the main console 110 can include a control system 112 and a display 114.

The camera 106 is configured to have a field of view covering the subject on the scan bed 102, and the camera 106 can be mounted, for example, on a ceiling above the scan bed 102, or at an upper part of an outer cover of the CT scan gantry 104 (higher than a position where the subject lies on the scan bed 102).

Figure 2:
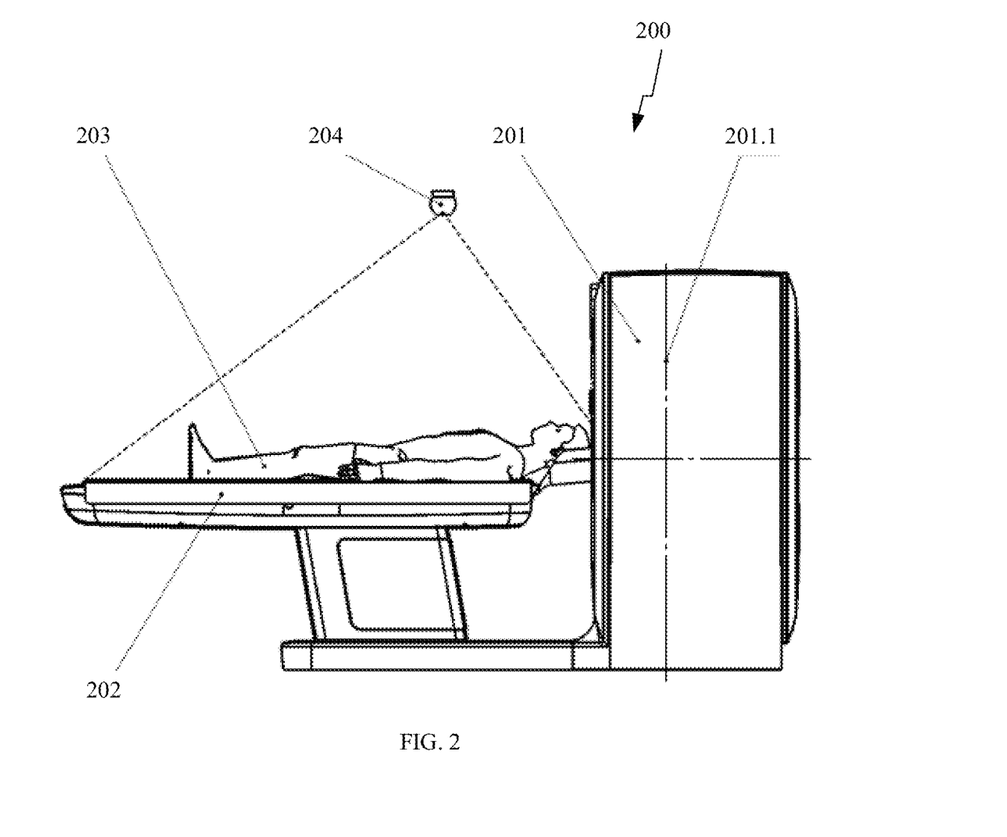
FIG. 2 is a side view illustrating a system for surview scan according to one or more embodiments of the present disclosure.
Figure 3:
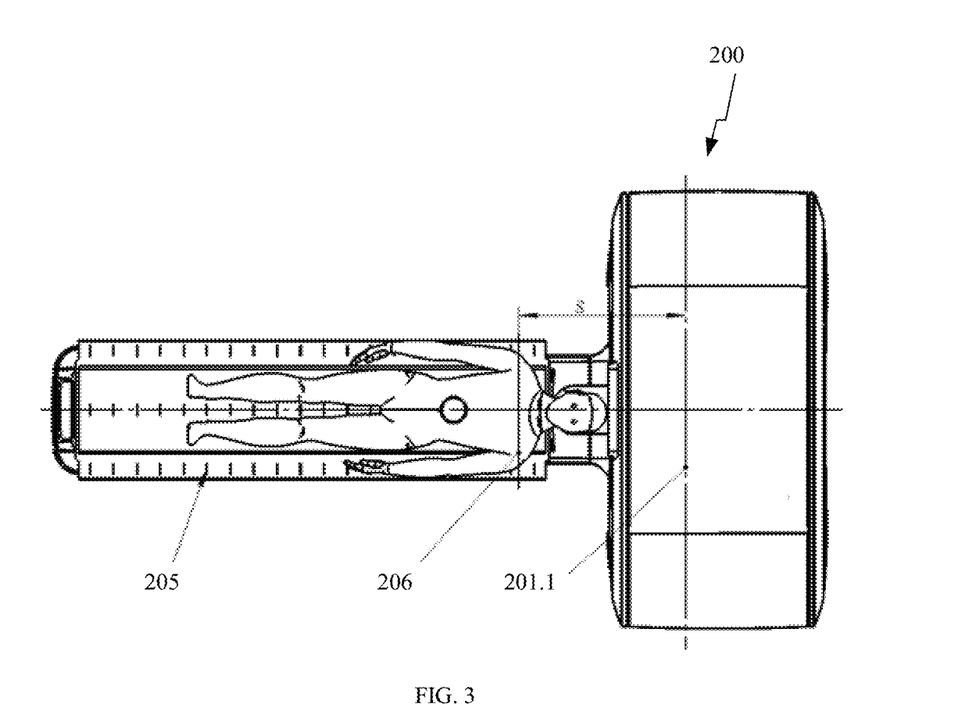
FIG. 3 is a top view illustrating the system for surview scan shown in FIG. 2.
Figure 4:
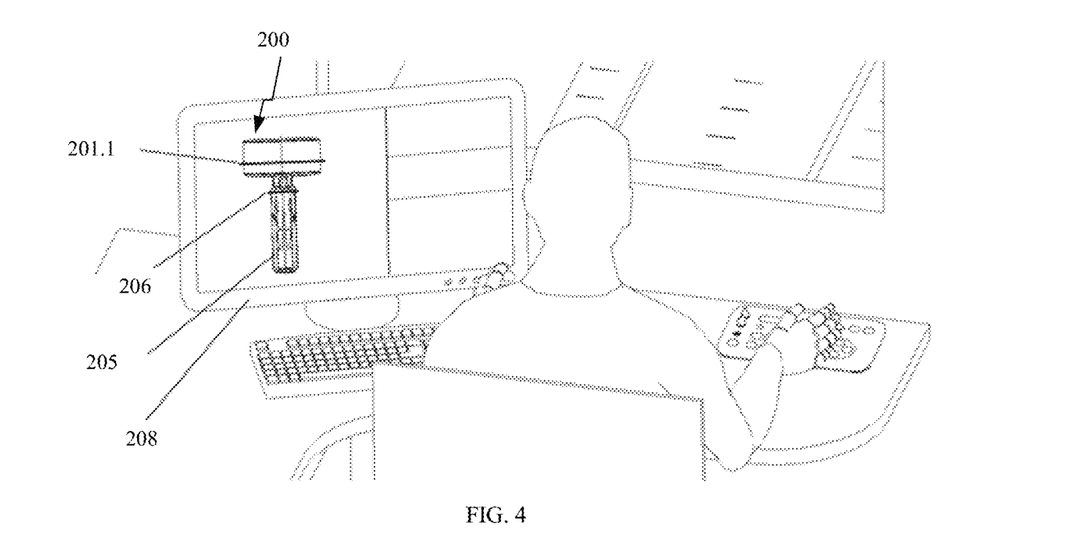
FIG. 4 is a displaying example diagram illustrating positioning lines in a screen of a main console according to one or more embodiments of the present disclosure.

FIGS. 2-4 illustrate a system 200 for surview scan according to one or more embodiments of the present disclosure, where FIG. 2 is a side view of the system 200, FIG. 3 is a top view of the system 200, and FIG. 4 is a displaying example diagram illustrating positioning lines in a screen of a main console of the system 200. The system 200 can be the system 100 of FIG. 1. In FIGS. 2, 3 and 4, reference numbers are list as below: scan gantry 201, surview collection plane 201.1, scan bed 202, subject 203, camera 204, graduation pattern 205, scan indication line 206 corresponding to a scan beginning position, and display 208. The surview collection plane 201.1 is perpendicular to the scan bed.

A method of surview scan according to the present disclosure will be described below in details in combination with the embodiments shown above.

Figure 5:
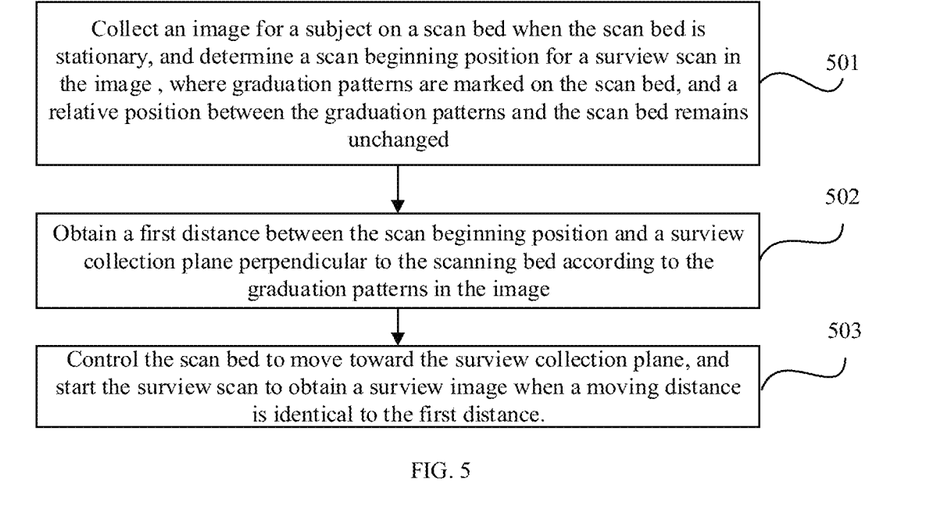
FIG. 5 is an example flowchart illustrating a method of surview scan according to one or more embodiments of the present disclosure.

FIG. 5 is an example flowchart of a process 500 illustrating a method of surview scan according to one or more embodiments of the present disclosure. The method of surview scan can be applied to a main console in a CT system or a PET-CT system. As shown in FIG. 5, in the embodiment, the process 500 can include steps 501-503. The CT system can be the system 100 of FIG. 1 or the system 200 of FIGS. 2-4. The process 500 can be performed by the main console, e.g., the main console 110 of FIG. 1 or the main console of FIGS. 2-4.

At step 501, an image for a subject (e.g., 203 of FIGS. 2-4) is collected when a scan bed (e.g., 102 of FIG. 1 or 202 of FIGS. 2-4) is stationary, and a scan beginning position for a surview scan is determined in the image, where graduation patterns (or scale patterns) (e.g., 205 of FIG. 3) are configured (e.g., marked) on the scan bed, and a relative position between the graduation patterns and the scan bed remains unchanged. The image can be collected by a camera, e.g., the camera 204 of FIG. 2.

At step 502, a first distance between the scan beginning position and a surview collection plane (e.g., 201.1 of FIGS. 2-4) perpendicular to the scanning bed is obtained according to the graduation patterns in the image. As illustrated in FIG. 4, an image shown on a display (e.g., 208 of FIG. 4) includes the graduation patterns (e.g., 205 of FIG. 4) and a surview collection plane (e.g., 201.1 of FIG. 4). The scan beginning position (e.g., scan indication line 206 of FIG. 4) can be determined in the image, and the first distance between the scan beginning position and the surview collection plane (e.g., distance S as illustrated in FIG. 3) can be determined based on the graduation patterns in the image, as illustrated in FIG. 4. In such a way, an operation technician in an operation room can determine the scan beginning position and the first distance without entering a scan room to be in direct contact with the subject, thereby reducing the risk to the health of the operation technician.

At step 503, the scan bed is controlled to move toward the surview collection plane. When a scan bed moving distance is identical to the first distance, the surview scan is started to obtain a surview image. That is, when the scan beginning position is in the surview collection plane, the surview scan is started.

In this embodiment, the graduation patterns are configured on the scan bed, and a relative position between the graduation patterns and the scan bed remains unchanged. In this way, according to graduation patterns corresponding to the scan beginning position in the image collected when the scan bed is stationary, the first distance between the scan beginning position before the scan bed moving and the surview collection plane can be obtained based on the image.

In some examples, the graduation patterns include graduation value information.

In some examples, the surview collection plane is a plane for performing surview scan and perpendicular to the scanning bed. The position of the surview collection plane is fixed. For example, the position of the surview collection plane can be determined according to a mounting position of a positioning lamp in a scan bore of a scan gantry of the CT system. When a part of the subject that needs to be surview scanned is located on the surview collection plane, a surview scan can be performed for the part to obtain a surview image. After obtaining the surview image, the CT system can complete position planning for a next tomography or helical scan based on the surview image.

In some examples, when the scan bed is stationary (prior to movement), a Z-direction distance (may also be abbreviated as a distance) between each graduation value (may also be referred to as scale value) and the surview collection plane is pre-configured. The Z-direction represents a movement direction of the scan bed. For example, the distance between the graduation value 0 and the surview collection plane is d0, and the distance between the graduation value 1 and the surview collection plane is d1 . . . , and so on.

After the subject lies on the scan bed, the camera in the CT system can collect video images of the subject and the scan bed in real time and send video images to the main console, and the main console displays the video images on a screen (a screen of the display of the main console), as shown in FIG. 4.

In an example, determining the scan beginning position for the surview scan in the image for the subject collected includes: determining the scan beginning position for the surview scan in the image according to received positioning operation information.

The positioning operation information can be input by a user. For example, in an application, a user (e.g., an operation technician) can click a scan beginning point in a video image for the subject collected in real time based on a to-be-scanned part of the subject, and the main console generates, based on the scan beginning point, a scan indication line (e.g., the scan indication line 206 shown in FIG. 3) passing through the scan beginning point and takes the scan indication line as a determined scan beginning position for surview scan.

The scan indication line is located in a plane parallel to the scan bed, and the scan indication line is perpendicular to a movement direction of the scan bed. In an example, to further distinguish a scan direction, the scan direction can be shown selectively on the display.

In above examples, the scan beginning position for surview scan is determined based on input such that the scan beginning position can be positioned more accurately, thus avoiding repeated scan and improving the scan efficiency.

In an example, determining the scan beginning position for the surview scan in the image for the subject includes: recognizing a face position in the image based on a predetermined face recognition algorithm, obtaining body height information of the subject according to one or more graduation patterns corresponding to the subject in the image, extracting a target scan region from a selected scan protocol, and determining, according to the recognized face position, the body height information and the target scan region, the scan beginning position for the surview scan in the image.

There is a certain proportional relationship among heights of various parts of a human body and the proportional relationship can be pre-stored in the system. According to a position of a body part and the proportional relationship, the position of other body parts related to the body part can be determined.

For example, it is assumed that, with a foot part as a beginning point, height proportions of a head and a heart in the human body are a and b respectively. In a case that an overall height and a head position (represented by a graduation value) of a person are determined, the position of the heart (represented by a graduation value) can be determined based on the proportional relationships a and b.

The face recognition algorithm can include, for example, an algorithm based on deep learning such as FaceNet algorithm, OpenFace algorithm, insightface algorithm, or DeepID algorithm, or an algorithm based on machine learning and conventional algorithm such as EigenFace algorithm, LBP algorithm, or AdaBoost algorithm.

In this embodiment, the scan beginning position is automatically determined based on the face recognition algorithm and the scan protocol, without requiring a user to making determination manually, thus further improving the degree of automation and increasing the scan efficiency.

The graduation patterns can be located on a bed board of the scan bed, or a mattress of the scan bed, or a mattress cover of the scan bed, or a bed cover of the scan bed.

In an example, the graduation patterns can be checkerboard patterns. In each of the checkerboard pattern, squares of two different colors are alternately disposed, and an intersection of adjacent squares is a graduation point corresponding to a graduation value.

Figure 6:
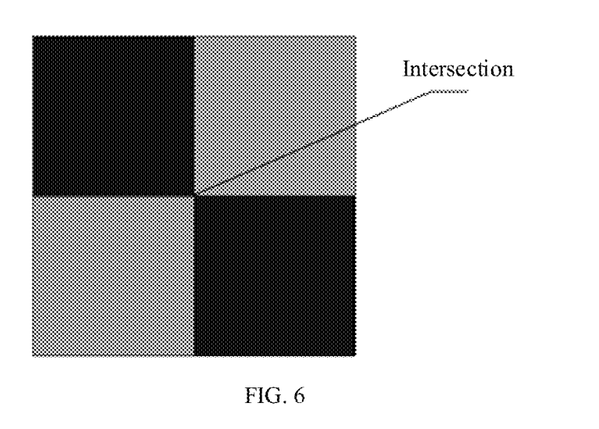
FIG. 6 is an example diagram illustrating one checkerboard pattern according to one or more embodiments of the present disclosure.

FIG. 6 is an example diagram illustrating a checkerboard pattern according to one or more embodiments of the present disclosure. As shown in FIG. 6, an intersection of black and white squares is a graduation point which can be clearly and accurately identified, thus avoiding mis-determination and improving the accuracy.

In an example, different graduation values of the graduation patterns correspond to different colors.

For example, graduation value 0 in the graduation patterns is yellow, graduation value 1 in the graduation patterns is red, graduation value 2 in the graduation patterns is blue, the graduation value 3 in the graduation patterns is green and the like. Further, a correspondence between a color and a graduation value is pre-stored in the system. In this case, when the color of the graduation patterns is identified in the image, the corresponding graduation value can be automatically determined.

In this embodiment, different graduation values correspond to different colors, the accuracy of identification of the graduation values can be improved, thereby avoiding mis-determination.

In an example, the method further includes: determining a scan ending position for the surview scan in the image, obtaining a second distance between the scan ending position and the surview collection plane according to the graduation patterns, starting the surview scan, controlling the scan bed to move toward the surview collection plane for the second distance and stopping the surview scan.

Figure 7:
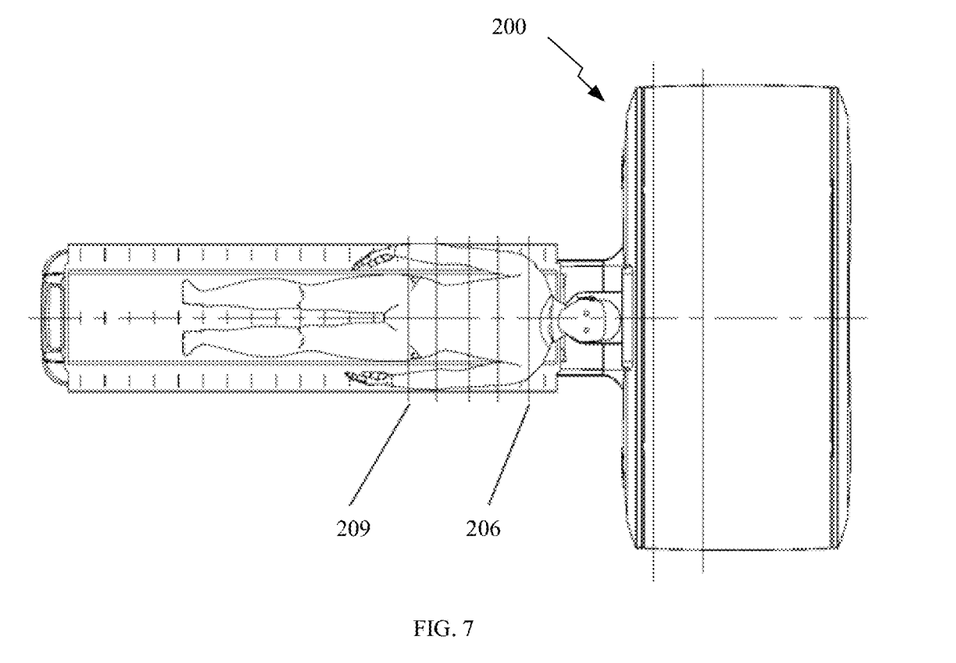
FIG. 7 is an example diagram illustrating a surview scan range according to one or more embodiments of the present disclosure.

FIG. 7 is an example diagram illustrating a surview scan range according to one or more embodiments of the present disclosure. As shown in FIG. 7, the scan ending position can be represented by a scan ending line 209 in FIG. 7 and a region between the scan ending line 209 and the scan indication line 206 is the surview scan range.

Similar to the determination of the scan beginning position, the scan ending position can also be determined in two manners. In a first determination manner, the scan ending position is determined by a user clicking a point in the image. In a second determination manner, a face position is recognized based on a face recognition algorithm, and a body height of the subject is obtained based on the graduation patterns corresponding to the overall height of the subject in the image, and then the scan ending position is automatically determined based on a face position according to a position relationship between a face and the scan ending position (the proportional relationship of each body part to the overall body height as mentioned above).

In this embodiment, a time of stopping the surview scan can be automatically determined and the surview scan can be automatically stopped, thus improving the degree of automation of a surview scan process.

In an example, the method further includes: determining a surview scan length according to a selected scan protocol; when a scan bed movement distance from starting the surview scan reaches the surview scan length, stopping the surview scan.

Before the surview scan is performed each time, a scan protocol is to be selected in advance. The scan protocol includes information of a surview scan length, such as chest length, and abdomen length. Therefore, the surview scan length can be obtained from the scan protocol.

The scan bed movement distance corresponding to a time when the surview scan is started is set to 0. Thus, when the scan bed movement distance reaches the surview scan length, a predetermined surview scan region has been scanned, and the surview scan can be stopped.

In this embodiment, a time of stopping the surview scan can be automatically determined and the surview scan is automatically stopped, thereby improving a degree of automation of a surview scan process.

In an example, obtaining the first distance between the scan beginning position and the surview collection plane according to the graduation patterns can include: in response to determining that one of the graduation patterns corresponding to the scan beginning position is not obstructed in the image, determining the first distance according to a position relationship between a graduation value of the one of the graduation patterns and the surview collection plane.

It can be known from the above content that the position relationship between each graduation value and the surview collection plane is fixed and thus the first distance can be directly determined based on the position relationship.

In an example, obtaining the first distance between the scan beginning position and the surview collection plane according to the graduation patterns includes: in response to determining that one of the graduation patterns corresponding to the scan beginning position is obstructed in the image, predicting a graduation value of the one of the graduation patterns according to one or more unobstructed graduation patterns in the image; determining the first distance according to a position relationship between the predicted graduation value and the surview collection plane.

In practical applications, the graduation patterns corresponding to the scan beginning position may be obstructed, and at this time, the graduation value of the graduation patterns corresponding to the scan beginning position cannot be visually determined, however, there are one or more unobstructed graduation patterns on the scan bed, and therefore, the graduation value of the graduation patterns corresponding to the scan beginning position can be automatically predicted based on the one or more unobstructed graduation patterns.

In practical applications, a scan indication line for indicating the scan beginning position and a scan ending line for indicating the scan ending position superimposed in the image can be extracted in real time. No limitation is made to the method of line extraction, for example, the extraction can be performed by using Hough Transform or any other line detection solution.

Through steps 501 and 502, a distance that the scan bed is to move from the scan beginning position to the surview scan plane can be automatically determined to provide basis for achieving automatic positioning.

It is noted that, in the embodiment of the present disclosure, it is not required to calibrate a camera coordinate system and/or a CT scan coordinate system, leading to easy and simple operation.

In a practical operation scenario, an operation technician opens a radiation shielding door of the operation room to allow the subject to enter the scan room on himself while the operation technician stays in the operation room. The operation technician can direct the subject to lie with a desired pose on the scan bed through a bidirectional talkback voice system and close the radiation shielding door remotely after the subject enters the scan room. In this process, the operation technician does not need to enter the scan room, thus reducing potential contact infection.

Afterwards, the operation technician can register the subject on the main console based on a scan examination sheet, or input relevant information of the subject through an information management system of a hospital, so as to complete the input of basic information such as name of the subject, and can further confirm the accuracy of the relevant information with the subject through the bidirectional voice system.

After completing these preparation works, the operation technician can start a system for surview scan to collect video images of the subject lying on the scan bed in real time and send the video images to the main console of the system, and the main console automatically completes surview scan according to the flow of the method of surview scan provided by the embodiments of the present disclosure.

The embodiments of the present disclosure can be applied to a CT system, or a Positron Emission Tomography Computed Tomography (PET-CT) system.

In the method of surview scan provided by the embodiments of the present disclosure, an image for a subject on a scan bed of a computed tomography system is collected when the scan bed is stationary, and a scan beginning position for a surview scan is determined in the image, where graduation patterns are marked in the scan bed, and a relative position between the graduation patterns and the scan bed remains unchanged; a first distance between the scan beginning position and a surview collection plane is obtained according to the graduation patterns in the image; the scan bed is controlled to move toward the surview collection plane; and when a moving distance of the scan bed is identical to the first distance, the surview scan is started to obtain a surview image. In this way, a time of starting the surview scan can be automatically determined based on the graduation patterns of the scan bed so as to complete the surview scan automatically without requiring the operation technician to enter the scan room to position the subject, thus avoiding contact infection. As a result, the health risk of the operation technician in a surview scan process is reduced.

Based on the above method embodiments, an embodiment of the present disclosure further provides corresponding apparatuses, devices and storage media.

Figure 8:
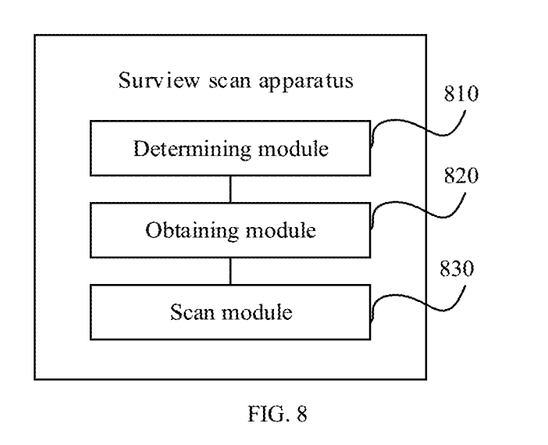
FIG. 8 is a diagram illustrating an apparatus for surview scan according to one or more embodiments of the present disclosure.

FIG. 8 is a diagram illustrating an apparatus for surview scan according to one or more embodiments of the present disclosure. As shown in FIG. 8, in this embodiment, the apparatus for a surview scan can include: a determining module 810, configured to collect an image for a subject on a scan bed of the computed tomography when a scan bed is stationary, and determine a scan beginning position for a surview scan in the image, where graduation patterns are marked in the scan bed, and a relative position between the graduation patterns and the scan bed remains unchanged; an obtaining module 820, configured to obtain a first distance between the scan beginning position and a surview collection plane perpendicular to the scanning bed according to the graduation patterns in the image; and a scan module 830, configured to, control the scan bed to move toward the surview collection plane, and in response to determining that a scan bed moving distance reaches the first distance, start the surview scan to obtain a surview image.

In an example, the apparatus further includes: an ending position determining module, configured to determine a scan ending position for the surview scan in the image; a second distance obtaining module, configured to obtain a second distance between the scan ending position and the surview collection plane according to the graduation patterns in the image; and a first stop controlling module, configured to, after starting the surview scan, control the scan bed to move toward the surview collection plane and then stop the surview scan in response to determining that a second scan bed moving distance reaches the second distance.

In an example, the apparatus further includes: a length determining module, configured to determine a surview scan length according to a selected scan protocol; a second stop controlling module, configured to, when a second scan bed movement distance from starting the surview scan reaches the surview scan length, stop the surview scan.

In an example, the determining module 810 can be configured to: determine the scan beginning position for surview scan in the image according to received positioning operation information.

In an example, the determining module 810 can be configured to: recognize a face position in the image for the subject based on a predetermined face recognition algorithm; obtain body height information of the subject according to one or more graduation patterns corresponding to the subject in the image; extract a target scan region from a selected scan protocol; determine, according to the recognized face position, the body height information and the target scan region, the scan beginning position for the surview scan in the image.

In an example, the obtaining module 820 can be configured to: in response to determining that one of the graduation patterns corresponding to the scan beginning position is unobstructed in the image, determine the first distance according to a position relationship between a graduation value of the one of the graduation patterns and the surview collection plane in the image.

In an example, the obtaining module 820 can be configured to: in response to determining that one of the graduation patterns corresponding to the scan beginning position is obstructed in the image, predict a graduation value of the one of the graduation patterns according to one or more unobstructed graduation patterns in the image; determine the first distance according to a position relationship between the predicted graduation value and the surview collection plane in the image.

In an example, the graduation patterns are checkerboard patterns, and in each of the checkerboard patterns, squares of two different colors are alternately disposed and an intersection of adjacent squares is a graduation point corresponding to a graduation value.

In an example, different graduation values of the graduation patterns correspond to different colors.

In an example, the graduation patterns can be located on a bed board of the scan bed, or a mattress of the scan bed, or a mattress cover of the scan bed, or a bed cover of the scan bed.

Figure 9:
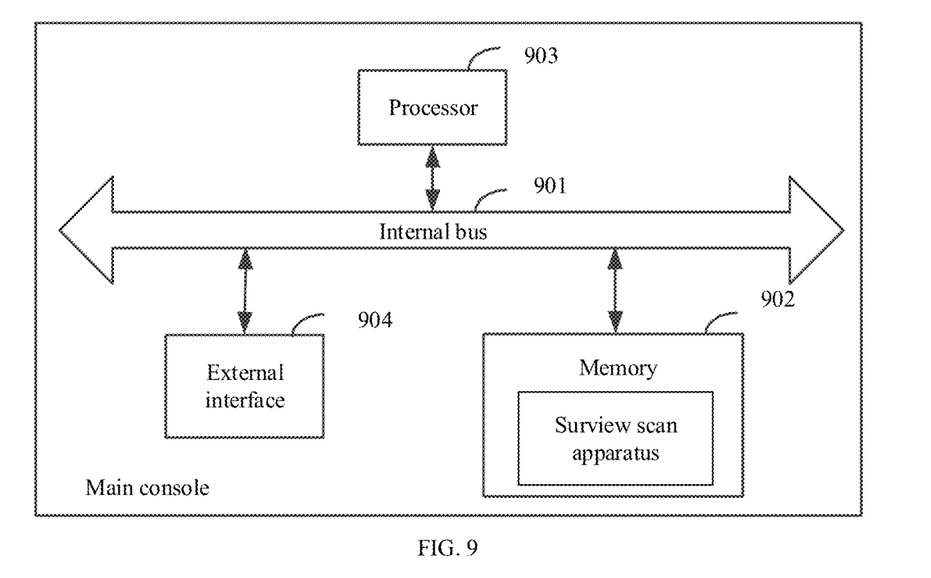
FIG. 9 is a hardware structure diagram illustrating a main console according to one or more embodiments of the present disclosure.

An embodiment of the present disclosure further provides a main console. FIG. 9 is a hardware structural diagram illustrating a main console according to one or more embodiments of the present disclosure. As shown in FIG. 9, the main console includes an internal bus 901, a memory 902, a processor 903 and an external interface 904, where the memory 902, the processor 903 and the external interface 904 are connected via the internal bus 901. The memory 902 is configured to store machine readable instructions corresponding to a surview scan logic; the processor 903 is configured to read the machine readable instructions in the memory 902 and execute the machine readable instructions to perform following operations: collecting an image for a subject on a scan bed of a computed tomography system when a scan bed is stationary; determining a scan beginning position for surview scan in the image, where graduation patterns are marked on the scan bed, and a relative position between the graduation patterns and the scan bed remains unchanged; obtaining a first distance between the scan beginning position and a surview collection plane perpendicular to the scanning bed according to the graduation patterns in the image; controlling the scan bed to move toward the surview collection plane; and in response to determining that a scan bed moving distance reaches the first distance, starting the surview scan to obtain a surview image.

An embodiment of the present disclosure further provides a computer readable storage medium storing computer programs thereon. The programs are executed by a processor to perform the following operations: collecting an image for a subject on a scan bed of a computed tomography system when a scan bed is stationary; determining a scan beginning position for surview scan in the image, where graduation patterns are marked on the scan bed, and a relative position between the graduation patterns and the scan bed remains unchanged; obtaining a first distance between the scan beginning position and a surview collection plane perpendicular to the scanning bed according to the graduation patterns in the image; controlling the scan bed to move toward the surview collection plane; and in response to determining that a scan bed moving distance reaches the first distance, starting the surview scan to obtain a surview image.

Since the apparatus and device embodiments substantially correspond to the method embodiments, a reference can be made to part of the descriptions of the method embodiments for the related part. The apparatus embodiments described above are merely illustrative, where the modules described as separate members can be or not be physically separated, and the members displayed as modules can be or not be physical modules, i.e., can be located in one place, or can be distributed to a plurality of network modules. Part or all of the modules can be selected according to actual requirements to implement the objectives of the solutions in the specification. Those of ordinary skill in the art can understand and carry out them without creative work.

The specific embodiments are described as above. Other embodiments can also be obtained within the scope of the appended claims. In some cases, the actions or steps recorded in the claims can be performed in a sequence different from the embodiments to achieve the desired result. Further, the processes shown in drawings do not necessarily require a particular sequence or a continuous sequence to achieve the desired result. In some implementations, a multi-task processing and parallel processing are possible and can also be advantageous.

Other implementations of the present disclosure will be apparent to those skilled in the art from consideration of the specification and practice of the present disclosure herein. The present disclosure is intended to cover any variations, uses, modification or adaptations of the present disclosure that follow the general principles thereof and include common knowledge or conventional technical means in the related art that are not disclosed in the present disclosure. The specification and embodiments are considered as exemplary only, with a true scope and spirit of the present disclosure indicated by the following claims.

It is to be understood that the present disclosure is not limited to the precise structure described above and shown in the accompanying drawings, and that various modifications and changes can be made without departing from the scope thereof. The scope of the present disclosure is limited only by the appended claims.

The foregoing disclosure is merely illustrative of preferred embodiments of the present disclosure but not intended to limit the present disclosure, and any modifications, equivalent substitutions, adaptations thereof made within the spirit and principles of the present disclosure shall be encompassed in the scope of protection of the present disclosure.

The invention claimed is:

1. A method applied to a computed tomography system, the method comprising:
   collecting an image for a subject on a scan bed of the computed tomography system when the scan bed is stationary;
   within the image, determining a scan beginning position for a surview scan, wherein graduation patterns are marked on the scan bed, and a relative position between the graduation patterns and the scan bed remains unchanged;

obtaining a first distance between the scan beginning position and a surview collection plane perpendicular to the scanning bed according to the graduation patterns in the image;

controlling the scan bed to move toward the surview collection plane; and in response to determining that a scan bed moving distance reaches the first distance, starting the surview scan to obtain a surview image;

wherein obtaining the first distance between the scan beginning position and the surview collection plane perpendicular to the scanning bed according to the graduation patterns in the image comprises:

in response to determining that one of the graduation patterns corresponding to the scan beginning position is unobstructed in the image, determining the first distance according to a position relationship between a graduation value of the one of the graduation patterns and the surview collection plane in the image.

2. The method of claim 1, further comprising:
determining a scan ending position for the surview scan in the image;
obtaining a second distance between the scan ending position and the surview collection plane according to the graduation patterns in the image; and
after starting the surview scan, controlling the scan bed to move toward the surview collection plane and then stopping the surview scan in response to determining that a second scan bed moving distance reaches the second distance.

3. The method of claim 1, further comprising:
determining a surview scan length according to a selected scan protocol; and
in response to determining that a second scan bed movement distance from starting the surview scan reaches the surview scan length, stopping the surview scan.

4. The method of claim 1, wherein determining the scan beginning position for the surview scan in the image comprises:
determining the scan beginning position for the surview scan in the image according to received positioning operation information.

5. The method of claim 1, wherein determining the scan beginning position for the surview scan in the image comprises:
recognizing a face position in the image based on a predetermined face recognition algorithm;
obtaining body height information of the subject according to one or more graduation patterns corresponding to the subject in the image;
extracting a target scan region from a selected scan protocol; and
determining, according to the recognized face position, the body height information and the target scan region, the scan beginning position for the surview scan in the image.

6. The method of claim 1, wherein the graduation patterns comprise checkerboard patterns, and in each of the checkerboard patterns, squares of two different colors are alternately disposed and an intersection of adjacent squares is a graduation point corresponding to a graduation value.

7. The method of claim 1, wherein different graduation values in the graduation patterns correspond to different colors.

8. The method of claim 1, wherein the graduation patterns are located on one of:
a bed board of the scan bed,
a mattress of the scan bed,
a mattress cover of the scan bed, or
a bed cover of the scan bed.

9. A system, comprising:
a scan bed;
a scan gantry;
a camera disposed above the scan bed; and
a main console,
wherein the scan gantry is configured to control the scan bed to move according to a control instruction of the main console,
wherein the camera is configured to collect a video image for a subject on the scan bed and send the video image to the main console, and p1 wherein the main console is configured to perform operations comprising:
collecting an image for the subject when the scan bed is stationary;
within the image, determining a scan beginning position for a surview scan, wherein graduation patterns are configured on the scan bed, and a relative position between the graduation patterns and the scan bed remains unchanged;
obtaining a first distance between the scan beginning position and a surview collection plane perpendicular to the scanning bed according to the graduation patterns in the image;
controlling the scan bed to move toward the surview collection plane; and
in response to determining that a scan bed moving distance reaches the first distance, starting the surview scan to obtain a surview image,
wherein obtaining the first distance between the scan beginning position and the surview collection plane perpendicular to the scanning bed according to the graduation patterns in the image comprises:
in response to determining that one of the graduation patterns corresponding to the scan beginning position is obstructed in the image, predicting a graduation value of the one of the graduation patterns according to one or more unobstructed graduation patterns in the image; and
determining the first distance according to a position relationship between the predicted graduation value and the surview collection plane in the image.

10. The system of claim 9, wherein the operations further comprise:
determining a scan ending position for surview scan in the image;
obtaining a second distance between the scan ending position and the surview collection plane according to the graduation patterns in the image; and
after starting the surview scan, controlling the scan bed to move toward the surview collection plane and then stopping the surview scan in response to determining that a second scan bed moving distance is identical to the second distance.

11. The system of claim 9, wherein the operations further comprise:
determining a surview scan length according to a selected scan protocol; and
in response to determining that a second scan bed movement distance from starting the surview scan reaches the surview scan length, stopping the surview scan.

12. The system of claim 9, wherein determining the scan beginning position for the surview scan in the image comprises:

determining the scan beginning position for the survey scan in the image according to received positioning operation information.

13. The system of claim 9, wherein determining the scan beginning position for the survey scan in the image comprises:
   recognizing a face position in the image based on a predetermined face recognition algorithm;
   obtaining body height information of the subject according to one or more graduation patterns corresponding to the subject in the image;
   extracting a target scan region from a selected scan protocol; and
   determining, according to the recognized face position, the body height information and the target scan region, the scan beginning position for the survey scan in the image.

14. The system of claim 9, wherein the graduation patterns comprise checkerboard patterns, and in each of the checkerboard patterns, squares of two different colors are alternately disposed and an intersection of adjacent squares is a graduation point corresponding to a graduation value.

15. The system of claim 9, wherein the graduation patterns are located on one of:
   a bed board of the scan bed,
   a mattress of the scan bed,
   a mattress cover of the scan bed, or
   a bed cover of the scan bed.

16. An electronic device, comprising:
   at least one processor; and
   one or more memories coupled to the at least one processor and storing programming instructions for execution by the at least one processor to perform operations comprising:
      collecting an image for a subject on a scan bed of a computed tomography system when the scan bed is stationary;
      within the image, determining a scan beginning position for a surview scan, wherein graduation patterns are marked on the scan bed, and a relative position between the graduation patterns and the scan bed remains unchanged;
      obtaining a first distance between the scan beginning position and a surview collection plane perpendicular to the scanning bed according to the graduation patterns in the image;
      controlling the scan bed to move toward the surview collection plane; and
      in response to determining that a scan bed moving distance reaches the first distance, starting the surview scan to obtain a surview image,
   wherein obtaining the first distance between the scan beginning position and the surview collection plane perpendicular to the scanning bed according to the graduation patterns in the image comprises:
      in response to determining that one of the graduation patterns corresponding to the scan beginning position is unobstructed in the image, determining the first distance according to a position relationship between a graduation value of the one of the graduation patterns and the surview collection plane in the image.

* * * * *